US00PP10804P

United States Patent [19]

Man

[11] Patent Number: Plant 10,804

[45] Date of Patent: Feb. 23, 1999

[54] BEGONIA PLANT NAMED 'DAISY FRANJE'

[75] Inventor: Jan Man, Amstelveen, Netherlands

[73] Assignee: Begonia Breeders Assoc., B.V., Aalsmeer, Netherlands

[21] Appl. No.: 923,728

[22] Filed: Sep. 4, 1997

[51] Int. Cl.[6] ..... A01H 5/00

[52] U.S. Cl. ..... Plt./87.18

[58] Field of Search ..... Plt./87.17, 87.18

[56] References Cited

U.S. PATENT DOCUMENTS

P.P. 10,519 7/1998 Man ..... Plt./87.18

*Primary Examiner*—Howard J. Locker
*Assistant Examiner*—Kent L. Bell
*Attorney, Agent, or Firm*—C. A. Whealy

[57] ABSTRACT

A distinct cultivar of Begonia plant named 'Daisy Franje', characterized by its attractive yellowish white semi- to fully double flowers that are fringed and about 6.5 cm in diameter; resistance to Powdery Mildew under commercial greenhouse conditions; and excellent postproduction longevity.

1 Drawing Sheet

The present invention relates to a new and distinct cultivar of Begonia plant, botanically known as *Begonia* X *hiemalis,* commercially known as Elatior Begonia, and hereinafter referred to by the cultivar name 'Daisy Franje'.

The new cultivar was discovered by the inventor in a controlled environment in Amstelveen, The Netherlands, in 1996, as a naturally-occurring mutation of the Elatior Begonia cultivar Clara Franje (U.S. Plant Pat. No. 10,519). The new cultivar was observed as a single plant in a group of 13-cm flowering plants of the parent cultivar. The selection of this plant was based on its yellowish white flower color compared to the very light greenish white flower color of the parent cultivar. A detailed comparison of plants of the new Begonia and the cultivar 'Clara Franje' appears in Chart A at the end of the specification.

Asexual reproduction of the new cultivar by terminal cuttings taken in a controlled environment in Amstelveen, The Netherlands, has shown that the unique features of this new Begonia are stable and reproduced true to type in successive generations.

The cultivar 'Daisy Franje' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Daisy Franje'. These characteristics in combination distinguish 'Daisy Franje' as a new and distinct cultivar:

1. Attractive yellowish white semi-double to double flowers that are fringed and about 6.5 cm in diameter.
2. Resistance to Powdery Mildew under commercial greenhouse conditions.
3. Excellent postproduction longevity.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical flowering plant of 'Daisy Franje'. Flower and foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Amstelveen, The Netherlands, that were flowered in June/July under commercial practice in a glass-covered greenhouse. Average day temperatures were 20° C. and average night temperatures were 18° C. The maximum light level was 18,000 lux. Measurements and numerical values represent averages for six typical flowering plants.

Botanical classification: *Begonia* X *hiemalis* cultivar 'Daisy Franje'.

Commercial classification: Elatior Begonia.

Parentage: Naturally-occurring mutation of *Begonia* X *hiemalis* cultivar 'Clara Franje', (U.S. Plant Pat. No. 10,519).

Propagation:

*Type.*—Terminal cuttings.

*Time to rooting.*—About 14 days with soil temperatures of 23° C.

*Rooting habit.*—Fine, fibrous and well-branched.

Plant description:

*Plant form.*—Upright and rounded potted plant, freely branching with good stem and stem base strength. Flowers are semi- to fully double and abundant. Plants flower continuously.

*Growth habit.*—Moderate growth rate and moderately vigorous. Suitable for 13-cm containers. Under optimal environmental and cultural conditions, usually 10 weeks are required to produce proportional 13-cm potted plants from terminal cuttings. Vegetative shoots are formed at basal nodes and flowering shoots are formed at upper nodes.

*Plant height.*—About 30 cm.

*Plant width.*—About 25 cm.

*Leaves.*—Arrangement: Simple, alternate. Length: About 17 cm. Width: About 12 cm. Shape: Asymmetrically ovate. Apex: Acute. Base: Cordate, overlapping. Margin: Slightly doubly serrate. Texture: Smooth, leathery, shiny. Color: Young foliage: Upper surface: 139A. Lower surface: 138B. Fully expanded foliage: Upper surface: 139A. Lower surface: 138B with red tones.

Flower description:

*Flowering habit.*—Semi- to fully double flowers arranged in axillary cymes. Many cymes in flower simultaneously. Flowering continuous.

*Natural flowering season.*—Plants will flower year around regardless of daylength, however plants will flower earlier and more abundantly if daylength is 12 hours or less. Usually plants start flowering after about 7 weeks of start of short day/long night treatments.

*Flowers.*—Shape: Rounded. Diameter: About 6.5 cm. Depth (height): About 1 cm.

*Tepals.*—Arrangement: Rosette. Shape: Mostly flat, rounded with fringed margin. Quantity per flower: Usually 10 to 25 per flower. Color: When opening: Upper surface: 2D. Lower surface: 2D. Fully opened: Upper surface: 2D. Lower surface: 2D. Texture: Smooth, velvety, glabrous.

*Sepals.*—Arrangement: Two, opposite. Color: 144A.

*Reproductive organs.*—Stamens: None. Pistils: None.

Postproduction longevity:

*Individual flowers.*—Generally 2 to 3 weeks.

*Whole plants.*—About 6 weeks under interior conditions.

Disease resistance: Plants of the cultivar 'Daisy Franje' are resistant to Powdery Mildew under greenhouse conditions.

Seed production: Seed production has not been observed as reproductive organs are not formed.

CHART A

| CHARACTERISTIC | 'DAISY FRANJE' | 'CLARA FRANJE' |
|---|---|---|
| YOUNG LEAF COLOR, UPPER SURFACE | 139A | 137B |
| YOUNG LEAF COLOR, LOWER SURFACE | 138B | 138B |
| FULLY EXPANDED LEAF COLOR, UPPER SURFACE | 139A | 139A |
| FULLY EXPANDED LEAF COLOR, LOWER SURFACE | 138B with red tones | 138B with red tones |
| FLOWER FORM | Semi- to fully double | Fully double |
| FLOWER DIAMETER | About 6.5 cm | About 6 cm |
| NUMBER OF TEPALS | 10 to 25 per flower | About 25 per flower |
| TEPAL COLOR, WHEN OPENING, UPPER SURFACE | 2D | 145D |
| TEPAL COLOR, FULLY OPENED, UPPER SURFACE | 2D | 157C/155B |
| TEPAL COLOR, FULLY OPENED, LOWER SURFACE | 2D | 157A to light green |

It is claimed:

1. A new and distinct cultivar of Begonia plant named 'Daisy Franje', as illustrated and described.

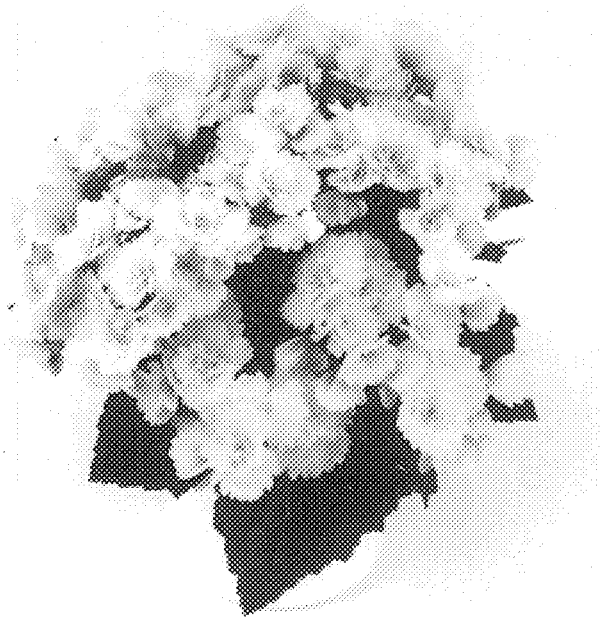

* * * * *